US009017733B2

(12) United States Patent
Bringley et al.

(10) Patent No.: US 9,017,733 B2
(45) Date of Patent: Apr. 28, 2015

(54) BIOACTIVE COMPOSITIONS

(76) Inventors: Joseph F. Bringley, Rochester, NY (US); Patrick M. Lambert, Rochester, NY (US)

( * ) Notice: Subject to any disclaimer, the term of this patent is extended or adjusted under 35 U.S.C. 154(b) by 233 days.

(21) Appl. No.: 13/806,765

(22) PCT Filed: Jun. 24, 2011

(86) PCT No.: PCT/US2011/001129
§ 371 (c)(1),
(2), (4) Date: Dec. 22, 2012

(87) PCT Pub. No.: WO2012/002996
PCT Pub. Date: Jan. 5, 2012

(65) Prior Publication Data
US 2013/0102684 A1 Apr. 25, 2013

Related U.S. Application Data

(60) Provisional application No. 61/360,522, filed on Jul. 1, 2010.

(51) Int. Cl.
| A61K 47/02 | (2006.01) |
| A61L 27/42 | (2006.01) |
| C03C 1/00 | (2006.01) |
| C03C 3/112 | (2006.01) |
| C03C 4/00 | (2006.01) |
| C03C 12/00 | (2006.01) |
| B82Y 5/00 | (2011.01) |

(52) U.S. Cl.
CPC ............... *A61K 47/02* (2013.01); *A61L 27/427* (2013.01); *C03C 1/006* (2013.01); *C03C 3/112* (2013.01); *C03C 4/0007* (2013.01); *C03C 12/00* (2013.01); *B82Y 5/00* (2013.01)

(58) Field of Classification Search
None
See application file for complete search history.

(56) References Cited

U.S. PATENT DOCUMENTS

| 3,592,832 A | 7/1971 | Yates |
| 5,074,916 A | 12/1991 | Hench et al. |
| 5,508,342 A | 4/1996 | Antonucci et al. |
| 5,952,399 A | 9/1999 | Rentsch |
| 6,653,043 B1 | 11/2003 | Hanabata |
| 7,090,720 B2 | 8/2006 | Kessler et al. |
| 2005/0260269 A1 | 11/2005 | Engelbrecht et al. |
| 2009/0227161 A1 | 9/2009 | Lambert |
| 2010/0016443 A1 | 1/2010 | Toledano et al. |

FOREIGN PATENT DOCUMENTS

WO    WO2006055317    *    5/2006

* cited by examiner

*Primary Examiner* — Robert A Wax
*Assistant Examiner* — Melissa Mercier
(74) *Attorney, Agent, or Firm* — Lynne M. Blank, Esq.

(57) ABSTRACT

The present invention relates to bioactive hetero-coagulated mixed materials that have high strength and durability, that are prepared using an aqueous process, and that have a high transparency when placed into a monomer, polymer, or resin of approximately the same refractive index.

22 Claims, No Drawings

BIOACTIVE COMPOSITIONS

CROSS REFERENCE TO RELATED APPLICATIONS

This application is the national phase application of PCT/US2011/001129, entitled "BIACTIVE COMPOSITIONS" filed on Jun. 24, 2011 under 35 U.S.C. 371, which claims priority to U.S. Provisional Patent Application Ser. No. 61/360,522 by J. Bringley et al., entitled "BIOACTIVE COMPOSITIONS AND METHODS OF PREPARATION", filed on Jul. 1, 2010, the disclosures of which are incorporated herein by reference.

FIELD OF THE INVENTION

The present invention relates to bioactive materials that have high strength and durability, that are prepared using an aqueous process, and that have a high transparency when placed into a monomer, polymer, or resin of approximately the same refractive index.

BACKGROUND OF THE INVENTION

Artificial biomaterials are introduced within the human body for repairing damages therein. The body conditions, however, are a severe environment and the combination of constant exposure to moisture, salt, biofluids, and continuous use over potentially decades provides a challenging environment. The body is also sensitive to foreign materials and may shows signs of poisoning, rejection and allergic responses.

All materials implanted within the body elicit a response from the surrounding tissue. "Bioactivity" is a unique property associated with the ability of materials that are foreign to the body to integrate and form a strong bond with living tissue. The interfacial bond may prevent rejection, accelerate the healing process, and increase the strength and durability of implants, devices, and/or repairs.

Bioactive materials include bioactive glasses, glass ceramics and ceramics. Bioactive ceramics are, for example, calcium phosphates and aluminum calcium phosphates and are used in orthopedic surgery. The most common problems with these materials relate to crystallization. The crystalline structure makes them difficult to work with and it is difficult to control the crystallization. The wear and degradation mechanisms, as well as durability of the ceramics, are not well understood. Bioactive glass ceramics are glassy materials having crystalline particles embedded in the amorphous glass phase. Ceravital is a glass ceramic that contains a glassy phase and an apatite crystalline phase.

Bioactive glasses, marketed as BIOGLASS, are amorphous materials. These materials encourage the growth of living bone onto their surfaces by slowly releasing calcium ($Ca^{2+}$) and phosphate ions ($PO_4^{3-}$) that are an essential part of the bodies bone building mechanism. Bioactive glasses have been in use for about 20 years as bone filling materials and prostheses in odontology, orthopedics and ophthalmology and some of the existing bioactive glasses can bond to both soft and hard tissue.

Three key compositional features distinguish bioactive glasses from traditional soda-lime-silica glasses. Conventional bioactive glasses typically contain less than 60 mole percent $SiO_2$, high $Na_2O$ and $CaO$ content (20-25% each), and a high molar ratio of calcium to phosphorus (ranging around five). Currently, bioactive powders are produced by conventional processing techniques well known in the art. The various constituents (for example, $Na_2CO_3$, $CaCO_3$, $P_2O_5$ and $SiO_2$) are usually mixed in a suitable mixing device, such as a rolling mill, and then heated in a platinum crucible to a temperature (generally between 1250 and 1400° C.) sufficient to cause the particles to melt and coalesce. The use of such high temperatures and specialized equipment results in significant production costs.

As pointed out by Hench et al. U.S. Pat. No. 5,074,916, conventional bioactive glasses suffer from other shortcomings. These compositions tend to require an alkali metal oxide such as $Na_2O$ to serve as a flux or aid in melting or homogenization. However, the presence of alkali metal oxide ions results in a high pH at the interface between the glass and surrounding fluid or tissue; in the body, this can induce inflammation. Furthermore, the rate of tissue repair, which drives the interfacial tissue-glass bonding promoted by the bioactive material, tends to vary within a narrow pH range. Conventional bioactive glasses also tend to be difficult to mix to homogeneity, a criterion that holds great importance for quality control of materials intended for implantation in the body. This is due to the relatively large grain size of the glass precursors, which generally measure approximately 10 to 1000 microns in diameter. It is difficult to obtain "molecular scale" mixing, i.e., homogeneity at the molecular level, using ordinary mixing techniques, such as stirring of the viscous glass melts.

Known bioactive glasses have attained clinical use as bone filling materials. They tend, however, to devitrify (crystallize) and their working range is narrow. Although the glasses are vitreous materials, some of them crystallize at low temperatures (about 600° C.). This makes them difficult to sinter into a product or to use for the manufacturing of spherical granules. They are often also phase separated due to their low content of silica, and the glass composition is therefore different from batch to batch.

The use of bioactive glasses is further restricted in applications where they are mixed as powders with biocompatible polymers to form a composite. The powders have a brittle or shard-like character and thus form an extremely abrasive surface that may cause irritation or excessive wear.

U.S. Pat. No. 5,508,342 to Antonucci et al. discloses a mineralizing agent for skeletal tissue comprising a mixture of an unsaturated monomer system, and a particulate mineralizing agent comprising amorphous calcium phosphate. However, amorphous calcium phosphates are brittle and have very poor strength and therefore are unsuitable in applications that require high-hardness, strength and toughness.

U.S. Pat. No. 5,952,399 to Rentsch, discloses a dental material based on an organic polymerizable binding agent, a polymerization catalyst, and relative to the dental material, 1-95 weight percent of an inorganic filler having a refractive index less than 1.58, wherein the filler comprises mixed-apatites, such as fluoroapatites, apatites containing sulfates and variations thereof. Rentsch contemplates significant chemical substitution of the hydroxyapatite lattice to adjust the refractive index from 1.63 to the preferred range near 1.52-1.56. Rentsch discloses compositions within or near this range, for example, $Ca_4Na_6(SO_4)F_2$; $\eta=1.52$, and $Ca_8Na_2[(PO_4)_4(SO_4)_2]F_2$; $\eta=1.57$. However, the disclosed materials have chemical compositions that are very different from hydroxyapatite and it is not clear if such materials are bioactive and may exchange $Ca^{2+}$ and $(PO_4)^{3-}$ ions with a biological environment. Further, fluoroapatites are very insoluble, have poor hardness and are brittle and therefore are unsuitable in applications that require high-hardness, strength and toughness.

WO 2006/055317A1 patent application to Rusin et al. discloses dental compositions and methods of making and using dental compositions that include a calcium and phosphorous releasing glass. However, as described above, bioactive glasses are difficult and expensive to prepare and have poor mechanical and abrasion wear properties.

U.S. Pat. No. 7,090,720 to Kessler et al. discloses a dental filling material for an aesthetic permanent dental filling, the dental filling material containing a resin matrix and up to 87 percent by weight of glass particles, wherein the glass particles have an average particle size less than 50 microns, the glass particles comprise bioactive glass particles and non-bioactive dental glass particles, the bioactive glass particles are capable of forming a hydroxyl apatite layer and comprise a bioactive glass material in which calcium is replaced in part with strontium and/or barium. Further, the resin matrix has an index of refraction approximately equal to an index of refraction of the bioactive glass particles and/or an index of refraction of the non-bioactive dental glass particles. However, as described above, bioactive glasses are difficult and expensive to prepare and have poor mechanical and abrasion wear properties.

U.S. Pat. No. 5,074,916 to Hench et al. discloses a bioactive composition prepared using a sol-gel process, and consisting essentially of more than 60 but no more than 86 weight percent $SiO_2$, at least 4 but less than 33 weight percent CaO and at least 3 but no more than 15 weight percent $P_2O_5$. The sol-gel process may form glasses at processing temperatures below the melt temperature of the glass. However, the process uses flammable hydrocarbon solvents, has a very low process yield and produces glasses with extremely high surface areas from about 200-500 $m^2$/g. The high surface area is problematic since it makes the materials very difficult to homogeneously disperse into polymers or monomers for the preparation of composites.

Problem to be Solved

There is a need therefore to produce bioactive materials that can be processed at lower temperatures and thus avoid the tendency to crystallize. There is a need to produce bioactive materials within a given particle size and surface area range that can be formulated into polymer composites without the abrasive character of the shard-like conventional glasses, or the handling difficulties of the sol-gel processed glasses. There is a need to produce bioactive materials that do not have high alkali metal contents. There is a need to produce bioactive materials that have a well defined and narrow dispersion of refractive index. There is a need to produce bioactive materials that have a high bioactivity and can be formulated into polymers, copolymers and other resins to make composites that are able to release $Ca^{2+}$ and $PO_4^{3-}$ ions at rates necessary to elicit a bioactive response in vivo.

SUMMARY OF THE INVENTION

The present invention relates to a composition comprising a bioactive hetero-coagulated mixed particle of at least one colloid chosen from the group consisting of silica, alumina, titania, zinc oxide, zirconia, and rare earth oxides, in combination with at least one soluble or insoluble bioactive material that contains calcium or phosphorus oxides or combinations thereof and a composition comprising a hetero-coagulated mixed particle of at least one colloid chosen from the group consisting of silica, alumina, titania, zinc oxide, zirconia, and rare earth oxides, in combination with at least one soluble or insoluble bioactive material that contains calcium or phosphorus oxides or combinations thereof dispersed in a matrix. The present invention also relates to a method comprising simultaneously combining at least one colloid chosen from the group consisting of silica, alumina, titania, zinc oxide, zirconia, and rare earth oxides, and a soluble or insoluble bioactive material comprising calcium or phosphorus oxides or combinations thereof in a high shear mixing zone to form bioactive hetero-coagulated mixed particles.

Advantageous Effect of the Invention

The present invention includes several advantages, not all of which are incorporated in a single embodiment. The invention herein discloses bioactive compositions that have a well defined and narrow dispersion of the refractive index, that have a high-bioactivity, that do not contain alkali metals, that have a spheroidal particle morphology and surface characteristics that enables them to be formulated into resin composites giving high-strength, toughness and wear abrasion properties. The invention also provides a method for producing bioactive compositions from aqueous solution and at low processing temperatures.

DETAILED DESCRIPTION OF THE INVENTION

The invention relates to a bioactive composition comprising a hetero-coagulated mixed particle of at least one colloid chosen from the group consisting of silica, alumina, titania, zinc oxide, zirconia, and rare earth oxides, in combination with at least one soluble or insoluble bioactive material that contains calcium or phosphorus oxides or combinations thereof. Preferably, the hetero-coagulated colloidal mixture is dried and thermally processed at a temperature below the melting temperature of the mixture.

Terms and Definitions.

Primary particle size is used herein to refer to the mean particle diameter of the aqueous colloids, or precipitated species, present in aqueous solution before thermal processing.

The term colloid as used herein refers to particles that form a stable suspension in a solvent or liquid medium such as water.

Surface functionalized particles as used herein refers to particles functionalized with inorganic, polymeric or molecular species.

Surface modified particles as used herein refers to surface functionalized particles which have been further reacted with other compounds bearing functional groups to produce a complex particle bearing a compound or compounds on its surface through the surface functionalization.

Hetero-coagulated as used herein refers to an assembly, grouping or aggregation of particles comprising two or more chemically distinct colloidal particle dispersions. The particles may assemble, group or aggregate by electrostatic attraction, by modification of surface charge or by a similar flocculation process.

The term bioactive as used herein refers to the ability of the inventive compositions, materials, particles or composites to integrate and form a strong bond with living tissue, to reduce inflammation and aid healing and, more specifically, to release calcium and phosphate ions within the body and promote the growth and/or remineralization of bone.

The inventive compositions are produced by the hetero-coagulation of colloids that are selected from at least one metal oxide and/or mixed metal oxides comprising the oxides of silicon, aluminum, titanium, zirconium, zinc and rare earths. It is possible to include also other metal oxides, and/or metal compounds such as hydroxides, carbonates, halides, phosphates, nitrates, etc. The colloids used in the invention are preferably selected from aqueous dispersible metal oxide particles including silica, alumina, zirconia, titania, zinc oxide and rare earth oxides. Most preferably, the colloids are silica, alumina, titania, zirconia, or combinations thereof. Specific examples include colloidal, precipitated or fumed silica, aluminas, such as $Al_2O_3$ and its polymorphs, AlOOH (also known as boehmite), zirconia, $ZrO_2$ or hydrous zirconias, rare earth oxides such as $Y_2O_3$ and $Yb_2O_3$, and the basic carbonates and nitrates of the aforementioned materials. A particularly preferred metal oxide is silica. The preferred silica particles are colloidal, precipitated or fumed silicas having the general formula $SiO_2$. Another particularly preferred embodiment is a silica colloid, and a second colloid.

The colloidal particles before hetero-coagulation are preferably stable aqueous colloids. A stable aqueous colloid is one that does not settle or separate from aqueous dispersion for a period of at least one month or more. It is preferred that the stable aqueous colloids have a mean particle diameter of between about 1 and 100 nm, more preferably between 1 and 50 nm and most preferred between 1 and 20 nm. The particle size(s) of the colloidal particles may be characterized by a number of methods, or combination of methods, including coulter methods, light scattering methods, sedimentation methods, optical microscopy and electron microscopy. Light scattering methods may sample $10^9$ or more particles and are capable of giving excellent colloidal particle statistics. Light scattering methods may be used to give the percentage of particles existing within a given interval of diameter or size, for example, 90% of the particles are below a given value. Light scattering methods can be used to obtain information regarding mean particle size diameter, the mean number distribution of particles, the mean volume distribution of particles, standard deviation of the distribution(s) and the distribution width for the particles.

The inventive compositions are produced by the hetero-coagulation of the metal oxide colloids with soluble or insoluble compounds that contain calcium or phosphorus oxides or combinations thereof. These compounds may be doped with other biologically relevant or advantageous ions, such as $Zn^{2+}$ and $Sr^{2+}$. The preferred calcium compounds may be selected from, but are not limited to, calcium halides, nitrates, oxides, carbonates, phosphates and calcium organic acid salts such as calcium acetate and calcium citrate. The preferred phosphorus oxides are phosphate, phosphite, hypophosphite or pyrophosphate salts of ammonium, hydrogen, sodium and potassium, most preferred are ammonium phosphates. Also preferred are organo-phosphorus compounds, such as triethyl phosphate, and the like. In a particularly preferred embodiment, the calcium and phosphate materials are insoluble particulates having a mean particle size diameter of less than 100 nm, and preferably less than 50 nm, most preferably less than 20 nm. The particularly preferred materials are amorphous and/or crystalline calcium phosphates having the chemical formulas $CaHPO_4$, $CaHPO_4.2H_2O$, $Ca_8(HPO_4)_2(PO_4)_4.nH_2O$, amorphous calcium phosphate, tricalcium phosphates, $Ca_5(PO_4)_3(OH)$, and fluoroapatites. In a particularly preferred embodiment, the calcium phosphate materials are $Ca_5(PO_4)_3(OH)$ and fluoroapatites having a primary particle size of less than 100 nm and more preferably less than 50 nm, most preferably less than 20 nm. Smaller particles are most preferred, because they allow the refractive index to be controlled precisely and also increase bioactivity, since the solubility, and, hence, the $Ca^{2+}$ and $PO_4^{3-}$ release rates, increases substantially as the size of the particles decrease below about 50 nm.

In the practice of the invention, the calcium phosphate particles may be formed in a separate step, prior to hetero-coagulation, and characterized and purified by methods common in the art. In this case, it is preferred that the calcium phosphate particles are stable aqueous colloids. It is preferred that the stable aqueous colloids have a mean particle diameter of between about 1 and 100 nm, more preferably between 1 and 50 nm, and most preferred between 1 and 20 nm. The preformed calcium phosphate particles may then be hetero-coagulated with the metal oxide colloids to prepare the bioactive hetero-coagulated particles. Alternatively, the calcium phosphate particles may be formed simultaneously with the hetero-coagulated colloid by precipitation in the presence of the other colloidal metal oxide materials. In this case, it is important to control the particle size and homogeneity of the hetero-coagulated mixed particles so that a material with a well-defined index of refraction is obtained.

The hetero-coagulation may be accomplished by mixing the selected colloids and calcium or phosphorus sources, such as phosphates, in a suitable solvent. The preferred solvent is water. The mixing may be accomplished by using a suitable mixing apparatus, such as a blade or prop-like stirrer or a magnetic stirrer. In a preferred embodiment, the mixing is accomplished by simultaneously adding the components into a high shear mixing zone. The high shear mixing zone may be provided by a propeller-like mixer, a static mixer, in-line mixers, dispersators, or other high shear mixing apparatus. The mixing efficiency of the apparatus is dependent upon the type of mixing method chosen and the precise geometry and design of the mixer. For propeller-like mixers, the mixing efficiency may be approximated by the turnover rate, where the turnover rate is the stir rate (rev/sec.) times the turnover volume (mL/rev) divided by the aqueous volume. For in-line or static mixers, the mixing efficiency may be approximated by multiplying the sum of the addition rates of the colloidal dispersions by the turnover volume of the mixer. In each case, the mixing efficiency has units of turnovers/sec. It is preferred that the mixing efficiency be greater than about 0.10 turnovers/sec. and, more preferably, greater than 1 turnover/sec. Complete mixing of the two solutions is preferably accomplished in less than about 10 seconds, and is more preferably accomplished substantially instantaneously.

The aqueous dispersions of the bioactive, hetero-coagulated mixed colloids of the invention, before drying or thermal treatment, are preferably stable colloidal dispersions. Colloidal stability refers to the ability of particles to remain stable in suspension (not to settle or separate from the dispersion). Aqueous dispersions of particles that remain in suspension for more than 30 days can be considered stable. The colloidal stability of dispersions may be determined by a number of methods. The dispersion may be placed in a tall, narrow glass container and the settling rate monitored visually over a period of months. A more quantitative approach is to measure the average particle size diameter of the particles in the dispersion. Unstable colloids show a tendency to aggregate or agglomerate, that is, particles begin to stick to one another. This aggregation is observed as an increase in the average particle diameter of the particles in the dispersion. Stable colloids show very little change in the average particle size diameter over a period of months and preferably over a period of greater than six months.

The aqueous dispersions of the bioactive, hetero-coagulated colloids of the invention are dried and thermally processed at a temperature below the melting point to produce homogeneous hetero-coagulated mixed particles of the colloid(s) and soluble or insoluble bioactive material. The drying and/or thermal processing may be accomplished in separate step, or combined into a single step. Drying may be accomplished by any convenient means, including drying the dispersion in a conventional oven, spray-drying, rotary drying, filtration, freeze-drying, or the like. The dried hetero-coagulated mixed particles are thermally processed at a temperature below the melting point of the mixture. The thermal processing step increases the homogeneity of the mixture, decreases the apparent surface area, and aids in the crystallization of the components. It is preferred that the thermal processing temperature is between about 200 to 1100° C., and more preferably from about 500-1000° C. During the thermal processing step, the particle components may aggregate or fuse together to form strong agglomerates. This reduces the surface area of the particles and increases their strength. It is preferred that the hetero-coagulated mixed particles, after thermal processing, have a specific surface area between about 5-200 m²/g and it is more preferred that the surface area is controlled to be from about 10-80 m²/g. The reduction in surface area facilitates the integration of the compositions of the invention into polymers, monomers, composites and other formulations, and also increases the mechanical strength of the composites made therefrom. It is further important that the surface area is not reduced to below about 5 m²/g, since low surface area materials have poor calcium and phosphate release properties and the bioactivity of the inventive compositions may be limited by the reduction in surface area.

After thermal processing, the hetero-coagulated mixed particles contain crystalline and/or amorphous materials. It is preferred that the hetero-coagulated mixed particles contain at least one crystalline or semicrystalline phase. It is also highly preferred that the crystalline or semicrystalline phases have a mean particle diameter less than about 50 nm and more preferably less than about 20 nm. The inclusion of small particles (<50 nm) within the hetero-coagulated mixed particles allows the refractive index of the hetero-coagulated mixed particles to be modulated, and to be tuned to a given value. The smaller the amorphous, crystalline, or semicrystalline inclusions, the less scatter of visible light, which allows the refractive index to be tuned to a precise value. Materials of known and narrow refractive index dispersion are particularly useful in optical applications and in applications where the aesthetic quality of a device, item or article is prized. It is preferred that the refractive index of the processed hetero-coagulated mixed particles is between about 1.46 and 1.60. This is preferred because it encompasses the refractive index range for a wide variety of polymers and monomers that are useful in optical, medical and coating applications.

In a preferred embodiment, the invention provides a bioactive material comprising a hetero-coagulated mixed particle that is prepared by simultaneously adding at least one colloid to soluble or insoluble calcium and phosphate containing materials, or combinations thereof, into a high shear mixing zone. Preferably, the hetero-coagulated mixed particles are made by simultaneously combining a silica colloid having a mean particle diameter of not more than 200 nm and a second colloid having a mean particle diameter of not more than 100 nm with a soluble or insoluble bioactive calcium or phosphorus containing material of combinations thereof. In another preferred embodiment, the hetero-coagulated mixed particles are made by simultaneously combining a silica colloid having a mean particle diameter of not more than 100 nm, a second colloid with a mean particle diameter of from 1 to 20 nm, and at least one bioactive material with a mean particle diameter of from 1 to 20 nm.

The method can further comprise drying the mixture to obtain a powder and thermally treating the dried powder. The resulting hetero-coagulated mixed particles are preferred to have an index of refraction between 1.46 and 1.60, and have a high transparency when dispersed in a fluid of substantially the same refractive index.

It is preferred that the transparency is as high as possible to facilitate optical and aesthetic applications of the materials of the invention. Transparency may be measured by any number of methods but is preferably measured by optical transmission spectroscopy. The inventive compositions are dispersed at a known weight fraction into a fluid of the same or nearly the same refractive index. The visible light transmission of the sample is measured at a given wavelength. The light transmission is dependent upon the thickness of the sample and the weight fraction of the solid phase. The weight fractions of the solid phase and sample thicknesses are held constant for comparison purposes. It is preferred that when the inventive composition is dispersed into a fluid of substantially the same refractive index at a volume fraction of at least 25%, the visible light transmission of a 1.5 millimeter thickness is greater than 25.0%. It is more preferred that the visible light transmission of a 1.5 millimeter thickness is greater than 50.0%

In order to facilitate the integration of the compositions of the invention into polymers, monomers, composites or other formulations, it may be necessary to modify the surfaces of the hetero-coagulated mixed particles with surface agents, for example, surfactants, coating aids, coupling agents, or the like. It is preferred that the particles have their surfaces modified by silane coupling agents, or hydrolyzed precursors of silane coupling agents having the general formula:

where a and b are integers from 1 to 3, (a+b) is less than or equal to 3, R and R' are organic groups having from 1-30 carbon atoms and R" is H, or an organic group having from 1 to 6 carbon atoms.

Alternatively, the silane coupling agent may have the general formula:

where a and R are as defined above and X is a halogen, Cl, Br or I.

Specific examples of silane coupling agents useful for practice of the invention include but are not limited to 3-mercaptopropyl(trimethoxy)silane, 3-mercaptopropylmethyl(diethoxy)silane, methacryloxypropyl(trimethoxy)silane, 2-[methoxy(polyethyleneoxy)propyl](trichloro)silane, 2-[methoxy(polyethyleneoxy)propyl](trimethoxy)silane, octyl(trimethoxy)silane, octadecyl(trimethoxy)silane, 3-isocyanatopropyldimethylchlorosilane, 3-isocyanatopropyl(triethoxy)silane, Bis(2-hydroxyethyl)-3-aminopropyltriethoxysilane, aminopropylsilanetriol, 3-aminopropyl(triethoxy)silane, 3-aminopropyl(trimethoxy)silane, N-(2-aminoethyl)-3-aminopropylsilanetriol, N-(2-aminoethyl)-3-aminopropyl(trimethoxy)silane, N-(2-aminoethyl)-3-aminopropylmethyldimethoxysilane, isopropyl(trimethoxy)silane, (3-glycidoxypropyl)methyldimethoxysilane, tetradecyldimethyl(3-trimethoxysilylpropyl)ammonium chloride, (3-trimethoxysilylpropyl)diethylenetriamine and octadecyldimethyl(3-ammonium)propyl(trimethoxy)silane.

To initiate the surface modification reaction, the particles and the surface agent(s) are mixed together in a high shear mixing zone within a dispersion medium. It is preferred that the dispersion medium is water, but other solvents or liquids may also be used.

In another embodiment, the hetero-coagulated mixed particles are dispersed within a matrix. The matrix may comprise at least one fluid, polymer, oligomer, monomer or combinations thereof. It is preferred that the inventive compositions are dispersed within the polymer, oligomer, or monomer at a loading of 1-60% by weight. It is preferred that the polymer, oligomer and/or monomer(s) is/are a thermally or light curable polymer. Useful examples of polymers are acrylate-functional materials, methacrylate-functional materials, epoxy-functional materials, vinyl-functional materials, and mixtures thereof. Typically, the hardenable resin is made from one or more matrix forming oligomer, monomer, polymer, or blend thereof. Also useful are urethanes, fluoropolymers, siloxanes and latex polymers.

In certain embodiments, the inventive materials are used in dental applications or in orthopedic or other in vivo applications. Polymerizable materials suitable for use in these applications include hardenable organic materials having sufficient strength, hydrolytic stability, and nontoxicity to render them suitable for use in the oral or in vivo environment. Examples of such materials include acrylates, methacrylates, urethanes, carbamoylisocyanurates, epoxies, and mixtures and derivatives thereof. One class of preferred hardenable materials includes materials having polymerizable components with free radically active functional groups. Examples of such materials include monomers having one or more ethylenically unsaturated group, oligomers having one or more ethylenically unsaturated group, polymers having one or more ethylenically unsaturated group, and combinations thereof.

In the class of hardenable resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth) acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone(meth)acrylamide; urethane (meth)acrylates and the bis-(meth)acrylates of polyethylene glycols. Other suitable free radically polymerizable compounds include siloxane-functional (meth)acrylates and fluoropolymer-functional (meth)acrylates. Mixtures of two or more free radically polymerizable compounds can be used, if desired.

Examples of other useful polymers include natural and synthetic biopolymers such as peptides, proteins, gelatin, poly(lactic acid), poly(glycolic acid), poly(caprolactone), chitosan and its derivatives, alginates and the like.

In another embodiment, the invention provides a bioactive composite or article comprising a bioactive composition that is prepared by the hetero-coagulation of colloids comprising at least one colloid chosen from silica, alumina, titania, zinc oxide, zirconia, or rare earth oxides; and soluble or insoluble compounds that contain both calcium and phosphorus oxides; wherein the hetero-coagulated colloidal mixture is dried and thermally processed at a temperature below the melting temperature of the mixture; and wherein the thermal processed hetero-coagulated mixed particle(s) is/are dispersed within a polymer, oligomer or monomer to form a composite; wherein the composite is bioactive and/or capable of leaching or exchanging $Ca^{2+}$ into an aqueous environment. The release of $Ca^{2+}$ is important since it stimulates the bodies own biological repair mechanisms. It is also desirable to exchange phosphate ions and silicate ions with the environment and, in particular, the in vivo environment. The release of calcium and other useful ions is facilitated by ion exchange with ions that are present in saliva, blood, or other biological fluids. It is imperative that the exchange is not too fast so as to quickly exhaust the supply in the biomaterial or not too slow such that the concentration of released ions is too low to stimulate the bodies biological repair mechanisms. It is preferred that the rate of release is controlled such that it may stimulate, in the case of medical applications, bone growth or bone adhesion; an in the case of dental applications such that it may affect the remineralization of tooth surfaces and protect teeth from demineralization. In order for biologically relevant concentrations of ions to be released from the composite, it is necessary for water to permeate the composite so that ion diffusion may occur.

In a particular embodiment it is preferred that the polymer (s), oligomer(s) or monomer(s) of the inventive composition are permeable to water. This is preferred because permeability facilitates the exchange of metal and other relevant ions between the biological environment and the article. A measure of the permeability of various polymeric addenda to water is given by the permeability coefficient, P, which is given by:

$$P = (\text{quantity of permeate})(\text{film thickness})/[\text{area} \times \text{time} \times (\text{pressure drop across the film})]$$

Permeability coefficients and diffusion data of water for various polymers are discussed by J. Comyn, in Polymer Permeability, Elsevier, N.Y., 1985 and in "Permeability and Other Film Properties Of Plastics and Elastomers", Plastics Design Library, NY, 1995. The higher the permeability coefficient, the greater the water permeability of the polymeric media. The permeability coefficient of a particular polymer may vary depending upon the density, crystallinity, molecular weight, degree of crosslinking, and the presence of addenda such as coating aids, plasticizers, etc. It is preferred that the polymer has a water permeability of greater than 10 $[(cm^3\ cm)/(cm^2\ sec/Pa)] \times 10^{13}$. It is further preferred that the polymer has a water permeability of greater than 100 $[(cm^3\ cm)/(cm^2\ sec/Pa)] \times 10^{13}$. The permeability of the composites of the invention can be optimized by one skilled in the art by mixing polymers and/or monomers that have different affinities for water. The hydrophilicity and hydrophobicity of the polymers, oligomers or monomers can be chosen to produce a given rate of $Ca^{2+}$ release.

For example, hydrophilic monomers can be blended into a formulation to increase the water permeability, whereas hydrophobic monomers will decrease permeability. Typical hydrophilic monomers useful for practice of the invention are 2-hydroxyethylmethacrylate, triethyleneglycoldimethacrylate, tetraethyleneglycoldimethacrylate and poly(ethylene glycol)dimethacrylates. Hydrophobic monomers and polymers suitable for practice of the invention include bis-GMA and hexanedioldimethacrylate.

EXAMPLES

The following examples are provided to illustrate the invention.

Materials

All material concentrations are given as a weight to weight percentage and all dispersions are in water, unless otherwise noted.

NALCO 2327 is a colloidal dispersion of silica in water; the mean silica particle diameter is 20 nm and the solids concentration 40.0%. NALCO 1050 is a colloidal dispersion of silica in water; the mean silica particle diameter is 20 nm and the solids concentration 50.0%. NALCO 1060 is a colloidal dispersion of silica in water; the mean silica particle diameter is 60 nm and the solids concentration 50.0%. NALCO 2329 is a colloidal dispersion of silica in water; the mean silica particle diameter is 75 nm and the solids concentration 40.0%.

Description of Testing Methods.

Calculation of Refractive Indices.

Refractive indices ($\eta_{tot}$) Were estimated for all compositions using the relationship given in equation 1.

$$\eta_{tot}=(\eta_1 V_1+\eta_2 V_2+\eta_3 V_3)/V_{tot} \quad (1)$$

where and $\eta_1$, $\eta_2$, and $\eta_3$ are the refractive indices of the individual components and $V_1$, $V_2$ and $V_3$ are the respective volume fractions of that component. The refractive indices used were the reported values; (1.46 for $SiO_2$, 2.11 for $ZrO_2$, 1.628 for $Ca_5(PO_4)_3(OH)$ and 1.675 for $Al_2O_3$). The volumes for each phase are calculated based on the weight percentages and densities of the components. (2.2 g/cm³ for $SiO_2$; 5.68 g/cm³ for $ZrO_2$; 3.6 g/cm³ for $Al_2O_3$, and 3.16 g/cm³ for $Ca_5(PO_4)_3(OH)$).

Optical Measurements.

The refractive index match and relative transparency in monomer fluids was determined by making mixtures of the mixed particles in a monomer of known refractive index at 25-35 wt %. The monomers were purchased from Sartomer Chemical or Esstech Inc. and are methacrylate monomers commonly used in dental restoratives. The mixtures were sonicated to remove air bubbles, and 3.08 g of the mixtures were added into a glass vials to a depth of 7.0 mm. The mixtures were placed on a light box and a series of optical targets were viewed by looking through the thickness of the sample. The mixtures were given a relative transparency score corresponding to the smallest font feature discernable (clearly visible and "readable"). Font sizes varied from 26-point to 2-point. For example, a rating of 1 indicates that only a 26-point font is readable, a score of 5 refers to readability of 18-point font or larger, 10=8-point and 13=2-point or larger. This simple qualitative method of determining transparency has an estimated accuracy of ± a score of 1. This method of ranking the relative transparency of the mixtures was validated using transmission spectrophotometry, (i.e., transmission correlated with rank). Refractive indices of the powders were approximated by placing the powders in a series of fluids of known refractive index and noting the highest transparency. Additional information can be found in U.S. Pat. Appl. entitled "Silica-Alumina Mixed Compositions" to P. Lambert et al., incorporated herein by reference in its entirety.

Preparation of Comparison Mixed Oxide (a).

Into a 2.0 L stainless steel reactor containing 300.0 g distilled water stirred with a prop-like mixer spinning at 2000 rpm, was simultaneously added: 640.0 g of colloidal silica (NALCO 1060; 50.0% silica solids) at a rate of 20.0 g/min; and 533.3 g of a 5-10 nm zirconia colloid (Nyacol Nanotechnologies, 20.0% zirconia solids) at a rate of 16.7 g/min. Throughout addition, 0.1 N acetic acid was added at a rate to keep the pH of the mixture between 4.0-4.4. Addition rates were controlled with peristaltic pumps that were precalibrated to control to within about ±0.1 g/min. After addition, the reaction mixture was allowed to stir for 1 hour. The suspension was then allowed to stand for 48 hours, after which time the mixture was translucent without any visible settling. After preparation, the product was dried in a forced air oven at 100° C., the solid obtained was milled with 9 mm alumina beads for 16 hours and the resulting fine powder was fired in a programmable furnace at 950° C. for 3 hours and allowed to cool. The white powder obtained was then sieved through a 100 micron nylon screen to remove any large particles.

Preparation of Hydroxyapatite Colloid (b).

Nanoparticulate hydroxyapatite was produced using the detailed procedure of Welzel et al. ("Transfection of Cells with Custom-made Calcium Phosphate Nanoparticles Coated with DNA", T. Welzel, W. Meyer-Zaika, R. Heumann and M. Epple, J. Mater. Chem. 14, 2213 (2004)). Into a 0.75 L stainless steel reactor containing 147.0 g distilled water and 3.0 g polyacrylic acid (MW 25,000 kDa, Wako Chemicals) stirred with a prop-like mixer spinning at 2000 rpm, was simultaneously added: 96.0 mL of a 0.50 M $Ca(NO_3)_2$ solution in which the pH was adjusted to 9.6, at a rate of 4.0 mL/min; and 96.0 mL of a 0.30 M $(NH_4)_2HPO_4$ solution in which the pH was adjusted to 9.6, at a rate of 4.0 mL/min. The pH after addition was 9.2. The stable translucent colloid was then dialyzed against distilled water for 48 hours to remove excess salts. The final percent solids of the colloid was determined to be 0.96 weight percent.

Inventive Example 1

Into a 0.75 L stainless steel reactor containing 150.0 g distilled water stirred with a prop-like stirrer spinning at 2000 rpm, was added 87.32 g of colloidal silica (NALCO 2327; 40.0% silica solids). After the suspension was allowed to stir for 10 minutes, was simultaneously added: 255 mL of 1.0M $Ca(NO_3)_2$ at a rate of 10.0 g/min; and 1 $NH_4OH$ solution to keep the pH between about 7.8 to 8.0. The ratio of silica to CaO in this example is 70:30 w/w. Addition rates were controlled with peristaltic pumps that were precalibrated to control to within about ±0.1 g/min. After addition, the reaction mixture was allowed to stir for 1 hour. After preparation, the product was dried in a forced air oven at 100° C., the solid obtained was milled using 9 mm alumina media for 24 hours and the resulting fine powder was fired in a programmable furnace at 550° C. for 3 hours and allowed to cool. The white powder obtained was then sieved through a 100 micron nylon screen to remove any large particles. The final molar composition was $(SiO_2)_{0.70}(CaO)_{0.30}$.

Inventive Example 2

Into a 0.75 L stainless steel reactor containing 150.0 g distilled water stirred with a prop-like stirrer spinning at 2000 rpm, was simultaneously added: 65.20 g of colloidal silica (NALCO 2327; 40.0% silica solids) at a rate of 7.3 g/min and 69.0 mL of 1.0M $Ca(NO3)_2$ at a rate of 10.0 g/min; and 1.0 N $NH_4OH$ solution to keep the pH between about 7.8 to 8.0 after addition, the pH was then adjusted to 9.2 through the addition of a 1.0 N $NH_4OH$ solution. To the stirred mixture was then added simultaneously: 197.2 mL of 1.0 M $Ca(NO3)_2$ at a rate of 1.7 g/min; and 118.4 mL of a 1.0 M $(NH_4)_2PO_4$ solution at 3.0 mL/min. Throughout addition the pH as adjusted to between about 8.8 to 9.2. through the addition of a 1.0 N $NH_4OH$ solution. After preparation, the product was dried in a forced air oven at 100° C., the solid obtained was milled using 9 mm alumina media for 24 hours and the resulting fine powder was fired in a programmable furnace at 550° C. for 3 hours and allowed to cool. The white powder obtained was then sieved through a 100 micron nylon screen to remove any large particles. The final molar composition was $(SiO_2)_{0.80}(CaO)_{0.12}[Ca_5(PO_4)_3(OH)]_{0.08}$.

Inventive Example 3

Into a 0.75 L stainless steel reactor containing 150.0 g distilled water stirred with a prop-like stirrer spinning at 2000 rpm, was simultaneously added: 71.20 g of colloidal silica (NALCO 2327; 40.0% silica solids) at a rate of 3.0 g/min and 183.3 mL of 1.0M $Ca(NO_3)_2$ at a rate of 10.0 g/min; and 1.0 N $NH_4OH$ solution to keep the pH between about 8.8 to 9.2. To the stirred mixture was then added simultaneously: 107.7 mL of 1.0M $Ca(NO_3)_2$ at a rate of 3.3 mL/min; and 64.6 mL of a 1.0 M $(NH_4)_2PO_4$ solution at 2.0 mL/min. Throughout addition the pH as adjusted to between about 8.8 to 9.2. through the addition of a 1.0 N $NH_4OH$ solution. After preparation, the product was dried in a forced air oven at 100° C., the solid obtained was milled using 9 mm alumina media for 24 hours and the resulting fine powder was fired in a programmable furnace at 550° C. for 3 hours and allowed to cool. The white powder obtained was then sieved through a 100 micron nylon screen to remove any large particles. The final molar composition was $(SiO_2)_{0.80}(CaO)_{0.27}[Ca_5(PO_4)_3(OH)]_{0.03}$.

Inventive Example 4 (AW BIOGLASS)

Into a 0.75 L stainless steel reactor containing 150.0 g distilled water stirred with a prop-like stirrer spinning at 2000 rpm, was simultaneously added: 46.50 g of colloidal silica (NALCO 2327; 40.0% silica solids) at a rate of 1.2 mL/min and; 303.4 mL of a mixture of 239.4 mL of 1.0 M $Ca(NO_3)_2$ and 64.0 mL of 1.0 M $Mg(NO3)_2$ at a rate of 1.0 mLg/min. The pH at the end of addition was 7.8. To the stirred solution was then added 0.474 g of $NH_4F$ dissolved in 10.0 mL of distilled water at a rate of 2.5 mL/min. To the stirred mixture was then added simultaneously: 152.8 mL of 1.0 M $Ca(NO_3)_2$ at a rate of 5.1 mL/min; and 91.67 mL of a 1.0 M $(NH_4)_2PO_4$ solution at 3.0 mL/min. Throughout addition the pH as adjusted to between about 8.8 to 9.2 through the addition of a 1.0 N $NH_4OH$ solution. After preparation, the product was dried in a forced air oven at 100° C., the solid obtained was milled using 9 mm alumina media for 24 hours and the resulting fine powder was fired in a programmable furnace at 550° C. for 3 hours and allowed to cool. The white powder obtained was then sieved through a 100 micron nylon screen to remove any large particles. The final molar composition was approximately $(SiO_2)_{0.47}(CaO)_{0.37}[Ca_5(PO_4)_3(OH)]_{0.09}(MgO)_{0.05}(CaF_2)_{0.02}$.

Inventive Example 5

Into a 0.75 L stainless steel reactor containing 150.0 g distilled water stirred with a proprietary mixer spinning at 2000 rpm, was simultaneously added: 195.67 g of colloidal silica (NALCO 2327; 40.0% silica solids) at a rate of 7.50 mL/min; and 79.4 g of a 5-10 nm zirconia colloid (Nyacol Nanotechnologies, 20.0% zirconia solids) at a rate of 4.0 mL/min. Throughout addition, 0.1 N acetic acid was added at a rate to keep the pH of the mixture between 4.0-4.4. Addition rates were controlled with peristaltic pumps that were precalibrated to control to within about ±0.1 g/min. After addition, the reaction mixture was allowed to stir for 1 hour. The solids content of the stable translucent silica-zirconia colloidal assembly was 9.52 weight percent.

Into a 0.75 L stainless steel reactor containing 130.0 g distilled water stirred with a prop-like stirrer spinning at 2000 rpm, was simultaneously added: 50.0 g of a mixture containing 37.06 g of the silica-zirconia colloidal assembly above and 12.94 g distilled water, at a rate of 2.5 mL/min; and 208.0 g of the hydroxyapatite colloid (b) at a rate of 10.4 mL/min. After the additions were complete, the product was dried in a forced air oven at 80° C.; the solid obtained was milled using 9 mm alumina media for 24 hours and the resulting fine powder was fired in a programmable furnace at 550° C. for 3 hours and allowed to cool. The white powder obtained was then sieved through a 100 micron nylon screen to remove any large particles. The final molar composition was $(SiO_2)_{0.86}(ZrO_2)_{0.11}[Ca_5(PO_4)_3(OH)]_{0.03}$.

Inventive Example 6

Performed in an identical manner as that of Example 5 except that the fine powder was fired at 750° C. for 3 hours and allowed to cool.

Inventive Example 7

Into a 0.75 L stainless steel reactor containing 150.0 g distilled water and 40.0 g of mixed oxide (a) with the molar composition $(SiO)_{0.86}(ZrO_2)_{0.14}$, and stirred with a prop-like stirrer spinning at 2000 rpm, was simultaneously added: (i) 42.9 mL of a solution of 1.0 M $Ca(NO_3)_2$ at 5.0 mL/min; and (ii) 28.6 mL of a 1.00 M solution of $(NH_4)_2HPO_4$ at 3.3 mL/min. The reaction feeds were controlled (+/−0.1 mL/min) and the pH held at 7.4 throughout by the addition of 0.1 N $NH_4OH$. After addition, the reaction mixture was stirred for 1 hour and the particles were collected and washed by centrifugation at 5,000 rpm for 5 min. and the supernatant discarded; this process was repeated four times to ensure complete removal of salt byproducts. The white powder obtained was then dried overnight in an oven at 100° C. Gravimetric determination indicated a yield of 99.6%. The final recovered composition contained approximately 90 wt. % $SiO_2$—$ZrO_2$ and 10 wt. % $Ca_5(PO_4)_3(OH)$.

Inventive Example 8

Into a 0.75 L stainless steel reactor containing 150.0 g distilled water and 40.0 g of mixed oxide (a) with the molar composition $(SiO)_{0.86}(ZrO_2)_{0.14}$, and stirred with a prop-like stirrer spinning at 2000 rpm, was simultaneously added: (i) 96.7 mL of a solution of 1.0 M $Ca(NO_3)_2$ at 5.0 mL/min; and (ii) 64.5 mL of a 1.00 M solution of $(NH_4)_2HPO_4$ at 3.3 mL/min. The reaction feeds were controlled (+/−0.1 mL/min) and the pH held at 7.4 throughout by the addition of 0.1 N $NH_4OH$. After addition, the reaction mixture was stirred for 1 h and the particles were collected and washed by centrifugation at 5,000 rpm for 5 min. and the supernatant discarded; this process was repeated four times to ensure complete removal of salt byproducts. The white powder obtained was then dried overnight in an oven at 100° C. Gravimetric determination indicated a yield of 99.3%. The final recovered composition contained approximately 80 wt. % $SiO_2$—$ZrO_2$ and 20 wt. % $Ca_5(PO_4)_3(OH)$.

Inventive Example 9

Into a 1.5 L stainless steel reactor containing 405 g of distilled water was added 245.5 g of 5-10 nm zirconia colloid (20.37 wt % ZrO2). Into this homogenized solution, 485.4 g of colloidal silica (NALCO 2327 41.2 wt. %, adjusted with glacial acetic acid to pH 5.5) was added at 10 mL/min into a prop-like mixer spinning at 2000 rpm. The resulting translucent stable colloid had a solids content of 22 wt. %.

Into a 4 L glass beaker containing 2250 mL of distilled water adjusted with 1 M NH4OH to pH 8.35, 579.5 g of the above colloid, diluted with distilled water to 1125 mL total volume, was simultaneously added into a prop-like mixer spinning at 2000 rpm, with 2344 g of hydroxyapatite prepared as for colloid (b). The silica-zirconia colloid was added at 10.87 mL/min and colloid (b) at 21.1 ml/min. During addition, the pH of the assembly solution was keep at pH 7.6 to 8.0. After completion of the additions, the product was dried at 100° C. for 20 hrs. The obtained solid was milled using 9 mm alumina beads for 24 hrs and the resulting powder heated at 900° C. for 3 hours. The resulting powder was sieved through a 100 micron screen. The final molar composition was $(SiO_2)_{0.87}(ZrO_2)_{0.11}[Ca_5(PO_4)_3OH]_{0.02}$.

The data of Table 1 shows the transparency index values obtained for examples and comparison examples 1-9. The hetero-coagulated mixed particles prepared from soluble $Ca^{2+}$ and $PO_4^{3-}$ sources show moderate to low transparency scores when placed into a fluid of approximately the same refractive index. Only Example 1 shows a transparency index above a value of 6 that is indicative of high transparency. The hetero-coagulated mixed particles prepared from insoluble or particulate calcium phosphates show very high transparency scores, well above 6 indicating that they have a well defined and sharp distribution of refractive indices.

TABLE 1

| Example | Calculated refractive Index | Fluid refractive index (1.542) | Fluid refractive index (1.523) | Fluid refractive index (1.534) |
| --- | --- | --- | --- | --- |
| 1 | 1.54 | 8 | Not measured | Not measured |
| 2 | 1.54 | 1 | Not measured | Not measured |
| 3 | 1.54 | 3 | Not measured | Not measured |
| 4 | 1.60 | 3 | Not measured | Not measured |
| 5 | 1.536 | 11 | 9 | 11.5 |
| 6 | 1.533 | 10 | 7.5 | 10.5 |
| 7 | 1.543 | 9 | Not measured | Not measured |
| 8 | 1.551 | 9 | Not measured | Not measured |
| 9 | 1.535 | Not measured | Not measured | 13 |
| Comparative Mixed oxide (a) | 1.535 | 9 | Not measured | Not measured |

The material from examples 1, 3 and 5-8 and the mixed oxide (a), as a comparison, were examined for assessment of cytotoxicity and bioactivity. In all experiments, the samples were compared to a negative control (no particles) and a positive control (pure nano-sized hydroxyapatite, evaluated as a standard for bioactivity). Cytotoxicity studies were performed using human dermal fibroblast cells and osteoblast adhesion and proliferation studies using nontransformed human osteoblasts (bone-forming cells). The cytotoxicity data are shown in Table 2. The cultures were exposed to doses of particulate materials of 1000 μg/mL. The data of Table 2 indicate that the mixed oxide (a) inhibits the growth of dermal fibroblast cells relative to the control and reference materials (note—the smaller the ratio of live/dead cells the greater the growth inhibition). This is indicative of very mild cytotoxicity. In contrast, the examples of the invention show equivalent or reduced inhibition relative to the reference and controls. The data show that the cytotoxicity of oxide materials can be improved by hetero-coagulation with bioactive materials such as calcium phosphates. Reduced cytotoxicity may translate to reduced inflammation and faster healing after an implant is place in vivo.

TABLE 2

Cytotoxicity of the examples and reference materials.

| | | Ratio of live to dead cells at time intervals | | |
| --- | --- | --- | --- | --- |
| Example | Exp. type | 1 day | 3 day | 5 day |
| 1 | example | 5.1 | 6.8 | 15.2 |
| 3 | example | 4.4 | 4.3 | 10.1 |
| 5 | example | 69 | 125 | 162.7 |
| 6 | example | 17.6 | 27.1 | 70 |
| 7 | example | 6.4 | 10.8 | 12.9 |
| 8 | example | 20 | 31.4 | 100.5 |
| No particles | reference | 224 | 136 | 156 |
| Commercial $Ca_5(PO_4)_3(OH)$ | control | 4.9 | 27 | 75.5 |
| Mixed oxide (a) | comparison | 1.9 | 1.3 | 1.2 |

TABLE 3

Osteoblast proliferation of the examples and reference materials.

| | | Cell Density (cells/cm$^2$) | | |
| --- | --- | --- | --- | --- |
| Example | Exp. type | 1 day | 3 day | 5 day |
| 1 | example | 2800 | 7300 | 9500 |
| 3 | example | 2900 | 7000 | 9000 |
| 5 | example | 3500 | 7400 | 9700 |
| 6 | example | 3400 | 8200 | 10,500 |
| 7 | example | 3800 | 6600 | 8800 |
| 8 | example | 4000 | 7500 | 9200 |
| No particles | reference | 3200 | 5300 | 6500 |
| Commercial $Ca_5(PO_4)_3(OH)$ | control | 3800 | 7200 | 8800 |
| Mixed oxide (a) | comparison | 3300 | 5000 | 7500 |

The results of osteoblast proliferation experiments are shown in Table 3. Osteoblasts are bone forming cells and their ability to adhere to and grow on a surface is indicative of the bioactivity of that surface. The materials, both examples and controls, were pressed into pellets prior to testing. Osteoblasts were seeded randomly onto the substrate surface, and cultured under standard cell culture conditions for 1, 3 and 5 day time periods. Osteoblast proliferation was assessed by measuring the amount of DNA in papin digests using Hoechst 33258 dye (Sigma) and a fluorospectrophotometer. The number of cells in the experimental samples was determined from a standard curve correlating the amount of DNA per known number of cells (assay sensitive to approximately 1,000). Proliferation is reported as cell density (cells per unit surface area cytotoxicity).

The data of Table 3 show that the inventive examples have significantly greater osteoblast growth rates compared to the reference, comparison and control materials. An increased cell density of osteoblasts is indicative of a bioactive surface.

The invention claimed is:

1. A composition comprising a bioactive hetero-coagulated mixed particle of at least one colloid chosen from the group consisting of silica, alumina, titania, zinc oxide, zirconia, and rare earth oxides, in combination with at least one soluble or insoluble bioactive material that contains calcium or phosphorus oxides or combinations thereof.

2. The composition of claim 1 wherein the at least one colloid is selected from the group consisting of silica, alumina, titania or zirconia having a mean primary particle size diameter of between 1 and 100 nm.

3. The composition of claim 1 wherein the at least one colloid comprises a silica colloid, and a second colloid.

4. The composition of claim 1 wherein the at least one colloid comprises a silica colloid having a mean particle diameter of not more than 200 nm, and a second colloid with a mean particle diameter not more than 100 nm.

5. The composition of claim 1 wherein the at least one colloid comprises a silica colloid having a mean particle diameter of not more than 100 nm, a second colloid with a mean particle diameter of from 1 to 20, and at least one bioactive material with a mean particle diameter of from 1 to 20 nm.

6. The composition of claim 1 wherein the at least one bioactive material comprises an insoluble calcium and phosphate containing material having a mean particle diameter of less than 100 nm.

7. The composition of claim 1 wherein the hetero-coagulated mixed particle has a specific surface area between 5 and 200 m$^2$/g.

8. The composition of claim 1 wherein the hetero-coagulated mixed particle contains at least one crystalline or semicrystalline phase.

9. The composition of claim 8 wherein the at least one crystalline or semicrystalline phase has a mean particle diameter of less than 50 nm.

10. The composition of claim 1 wherein the hetero-coagulated mixed particle has a refractive index between 1.46 and 1.60.

11. The composition of claim 1 wherein the hetero-coagulated mixed particle is functionalized with a surface agent to produce surface functionalized particles.

12. The composition of claim 11 wherein the surface agent comprises silane coupling agents, or hydrolyzed precursors of silane coupling agents having the general formula:

$$R_a R'_b Si(OR'')_{4-(a+b)},$$

where a and b are integers from 1 to 3;
(a+b) is less than or equal to 3;
R and R' are organic groups having from 1-30 carbon atoms; and
R'' is H, or an organic group having from 1 to 6 carbon atoms.

13. The composition of claim 11 wherein the surface agent comprises silane coupling agents, or hydrolyzed precursors of silane coupling agents having the general formula:

$$R_a Si(X)_{4-a},$$

where a is an integer from 1 to 3;
R is an organic group having from 1-30 carbon atoms; and
X is a halogen, Cl, Br or I.

14. A composition comprising a hetero-coagulated mixed particle of at least one colloid chosen from the group consisting of silica, alumina, titania, zinc oxide, zirconia, and rare earth oxides, in combination with at least one soluble or insoluble bioactive material that contains calcium or phosphorus oxides or combinations thereof dispersed in a matrix.

15. The composition of claim 14 wherein the matrix comprises at least one member selected from the group consisting of fluid, polymer, oligomer, or monomer.

16. The composition of claim 15 wherein the composition has an index of refraction between 1.46 and 1.60.

17. The composition of claim 16 wherein the visible light transmission of a 1.5 millimeter thickness is greater than 25.0%, when the hetero-coagulated mixed particle is dispersed within a fluid of substantially the same refractive index at a volume fraction of at least 25%.

18. The composition of claim 16 wherein the visible light transmission of a 1.5 millimeter thickness is greater than 50.0%, when the hetero-coagulated mixed particle is dispersed within a fluid of substantially the same refractive index at a volume fraction of at least 25%.

19. The composition of claim 14 wherein the composite is bioactive and/or capable of leaching or exchanging Ca$^{2+}$ into an aqueous environment.

20. The composition of claim 15 wherein the hydrophilicity and hydrophobicity of the polymer, oligomer or monomer is chosen to produce a given rate of Ca$^{2+}$ release.

21. A method comprising simultaneously combining at least one colloid chosen from the group consisting of silica, alumina, titania, zinc oxide, zirconia, and rare earth oxides, and a soluble or insoluble bioactive material comprising calcium or phosphorus oxides or combinations thereof in a high shear mixing zone to form bioactive hetero-coagulated mixed particles.

22. The method of claim 21 further comprising:
   b. drying the hetero-coagulated mixed particles to obtain a powder; and
   c. thermally treating the dried powder, wherein the hetero-coagulated mixed particles are dried and thermally treated at a temperature below the melting temperature of the mixed particles.

* * * * *